United States Patent [19]
Mandler et al.

[11] Patent Number: 5,573,698
[45] Date of Patent: Nov. 12, 1996

[54] RETURNABLE CONTAINER CONTAINING DETERGENT, CLEANING AGENT, DISINFECTANT AND/OR PRESERVATIVE

[75] Inventors: Gunter Mandler, Heuchelheim; Wolfram Rieber, Neuhofen; Richard Sander, Pfinztal-Berghausen; Jürgen Kompan, Römerberg, all of Germany

[73] Assignee: Ecopack GmbH & Co., Heuchelheim, Germany

[21] Appl. No.: 290,852

[22] PCT Filed: Nov. 5, 1992

[86] PCT No.: PCT/EP92/02540

§ 371 Date: Oct. 24, 1994

§ 102(e) Date: Oct. 24, 1994

[87] PCT Pub. No.: WO93/16166

PCT Pub. Date: Aug. 19, 1993

[30] Foreign Application Priority Data

Feb. 14, 1992 [DE] Germany .................. 42 04 489.8

[51] Int. Cl.⁶ .................. C11D 17/00; B65D 21/04; B65D 85/84

[52] U.S. Cl. .................. 510/277; 252/380; 206/503; 206/515; 206/519; 206/524.1; 220/770; 220/771; 510/224; 510/295; 510/439

[58] Field of Search .................. 252/90, 91, 174; 206/503, 515, 524.1, 519; 220/770, 771

[56] References Cited

U.S. PATENT DOCUMENTS

| Re. 32,818 | 1/1989 | Fernholz et al. | 252/90 |
|---|---|---|---|
| 4,808,236 | 2/1989 | Davis, Jr. | 134/25.2 |
| 4,999,124 | 3/1991 | Copeland | 252/90 |
| 5,086,952 | 2/1992 | Kryk | 222/189 |
| 5,186,912 | 2/1993 | Steindorf et al. | 422/263 |
| 5,198,198 | 3/1993 | Glapfelter et al. | 422/264 |
| 5,316,688 | 5/1994 | Gladfelter et al | 252/90 |

*Primary Examiner*—Paul Lieberman
*Assistant Examiner*—Lorna M. Douyon
*Attorney, Agent, or Firm*—Hill, Steadman & Simpson

[57] ABSTRACT

A product dispense package suitable for employment in washing machines, comprises a stackable product container which includes a unitary molded recyclable thermoplastic container body having a closed bottom end, an opposed open top end and an upwardly and outwardly angled upstanding peripheral side wall having a stacking angle of from about 2° to about 7° and contained therein a compact block of detergent, cleaning agent, disinfectant and/or preservative having a powdery structure. The bottom end includes an inwardly and upwardly directed dome-shaped region therein including a handle grip portion defined in an outwardly facing side of the dome-shaped region.

11 Claims, 15 Drawing Sheets

RETURNABLE CONTAINER CONTAINING DETERGENT, CLEANING AGENT, DISINFECTANT AND/OR PRESERVATIVE

BACKGROUND OF THE INVENTION

The invention is directed to the subject matter recited in the patent claims. In particular, the invention is directed to a method for manufacturing pressed, shaped and at least partially porously fashioned detergent, cleaning agent, disinfectant and/or preservative without employing a pre-heated melt or solution, whereby a pre-fabricated premix composed of powdered and/or granulated active ingredients manufactured with or without mixing this prefabricated mixture with a binder is filled into a suitably shaped, shape-stable, stackable and refillable returnable container without undercuts and is compressed under pressure, so that a compact block having powder structure consolidated in the container is formed.

The invention is also directed to recyclable, upwardly open as well as conically upwardly expanding returnable containers that can be utilized for liquid, solid or, respectively, powdered detergent, cleaning agent, disinfectant and/or preservative and that, in particular, can be utilized in dishwashers and washing machines for the implementation of the afore-mentioned method. In particular, the invention is directed to reemployable or, respectively, recyclable returnable containers particularly suitable for employment in washing machines that contain detergent, cleaning agent, disinfectant and/or preservative, said returnable containers being fashioned such that detergent, cleaning agent, disinfectant and/or preservative is delivered from the container when a stream of aqueous liquid is placed on a surface of the detergent, cleaning agent, disinfectant and/or preservative exposed to said stream of aqueous liquid. The invention, finally, is directed to the employment of this returnable container. It is critical for the container of the invention including the cover thereof that both the filled and closed container as well as the empty container and the cover is (are) fashioned stackable in and of itself (themselves).

Advantageous embodiments of the invention are contained in the subclaims.

In addition to liquid, paste-like or powdered detergents, shaped, piece-shaped, solid detergent products have been known and in use for a long time such as, for example, bars of soap, syndet bars of soap, toilet cones or tablets, shaped detergents for dishwashers and washing machines, etc.

A general overview is contained, for example, in the publication by H. E. Tschakert, "Seifen", Oele, Wachse, 98 (1972) 793–801, 845–849 and Ibid. 99 (1973) 3–7.

In addition to the manufacture of such shaped, piece-shaped detergent products by pressing and extruding processes (to form tablets, briquettes and the like), manufacture by pouring a solution or melt capable of solidification into forms has been standard for a long time, this having the advantage compared to pressing that complicated and, for example, irregularly structured shaped pieces can also be manufactured in a simple way.

The solution or melt is frequently poured into the molds in the heated condition in this case and they solidify when cooled.

The shaped pieces can either be removed from the molds after the solidification and can reach the user in a separate packing or, on the other hand, the container employed as mold simultaneously serves as packaging for the shaped detergent piece and reaches the user connected thereto, whereby the amount of detergent required for the respective use in every employment is generally released from the shaped, piece-shaped detergent product in its envelope due to the action of corresponding solvents, usually water.

Examples of such product formulations and manufacturing methods are recited, for example, in Tenside 8 (1991) 275, in Tenside 11 (1974) 330, in Seife, Oele, Fette, Wachse 96, No. 23 (1970) 823 as well as, in particular, in the afore-mentioned publication by H. E. Tschakert.

Likewise, the "Jahrbuch fuer den Praktiker", Verlag fuer Chem. Ind. Ziolkowski, Augsburg, 1972, p. 194, 1973, p. 229, 1974, p. 110 and pp. 132, 134, 135, 1975, pp. 116, 117, 118, 1976, pp. 116–120, which is well-known to a person skilled in the art active in this field provides various exemplary formulations for shaped detergent pieces that are manufactured by pouring a heated melt or, respectively, solution into molds and by solidification during cooling.

Recently, patent literature has also concerned itself with the method for manufacturing shaped, solid cleaning agents by filling a heated melt or, respectively, solution into molds and solidification during cooling; thus, for example, European patent application 0 003 769, European patent application 0 307 587, pouring alkaline aqueous solution, as well as German patent applications DE 35 19 353, DE 35 19 354, DE 35 19 355, DE 36 34 812.

All of these published manufacturing methods for solid, shaped detergent members are affected by production-related or qualitative disadvantages, since a) only specific, simple molds can be produced in the case of manufacture by pelleting, briquetting, etc., and extremely complicated systems are also required for processing;

b) considerable energy is required for melting the initial mixtures and keeping them warm in the case of manufacture on the basis of pouring a melt or heated solution into a mold and thermally sensitive constituents of the formula suffer increased damage or, respectively, a higher degree of degradation or, respectively, decomposition as a consequence of the dwell at a higher temperature that necessary lasts a longer time than if no heating or only an extremely brief-duration heating were to occur.

EP-A-0242966 shows the solidification of a granular detergent mixture in a container by pouring an aqueous solution in that is heated to more than 66° C. through 83.5° C., this then filling the interspace from top to bottom without agitation.

This procedure has the disadvantage that an excessively rapid solidification of the upper part in the mixture in the container easily ensues upon initial contact of the impregnating liquid with the podwer mixture, so that the liquid does not or does not adequately impregnate the lower parts of the mixture, particularly when fine constituents are present due to abrasion, and an incomplete formation of a block occurs in this way.

EP-A-0 375 022 discloses a detergent pellet that has been pressed under extremely high pressure (3–30 KN/cm$^2$). Such detergent can then be employed for commercial dish washing.

U.S. Pat. No. 4,808,236 discloses the manufacture of a piece-shaped detergent product by pouring a solution capable of solidification or a melt into a form. This solution or melt then solidifies upon cooling and remains in the container employed as mold.

WO 89/11753 is directed to shaped detergent pieces that contain pre-shaped chlorine cores or sources. These shaped pieces are manufactured by pouring a solution capable of solidification into a mold. The shaped pieces are in turn removed from the mold after solidification and can be utilized in dishwasher machines at low water temperatures.

The Derwent abstract of JP-A-1161100 discloses a detergent mixture packed in a container that has a high bulk density (0.5–1.2 g/cm$^2$).

EP-A-0 225 859 discloses a dosing apparatus for dissolving detergents. A block detergent product is introduced into a housing, this product then being sprayed from below with a nozzle, so that the detergent can proceed via a conduit into the rinsing water. The containers for the block or briquette product are cylindrically fashioned and have a foil covering at their upper end.

As stated above, specific containers are utilized as mold or as packaging of the detergent, cleaning agent, disinfectant and/or preservative. In Germany and Europe, however, there is a requirement to the effect of designing or, respectively, utilizing reemployable containers whose raw material, moreover, is also recyclable.

Due to increasing quantities of garbage, there is an increased need for packaging systems that manage with optimally small packaging volumes relative to the filling quantity. Over and above this, the requirement is directed to mono packaging materials that can be simply are reliably completely emptied, particularly when filled with hazardous substances. One possibility for chemical products such as, for example, cleaning agents is comprised in filling with concentrates instead of highly dilute mixtures. Reductions in the need for packaging material of factors of 2–5 should be possible here in the field of cleaning agents. A further reduction is conceivable by employing returnable containers with which reduction factors of 5–10 are again possible. A few important demands, however, must be satisfied for returnable containers of this product group:

1. Complete, optimally simple residual emptying before being returned for refilling (because of unproblematical transport and contamination-free refilling).
2. Designing the product containers in such a way that, in their emptied condition, these become reducible in terms of volume by a reduction factor of approximately five (transport costs are calculated based on volume).
3. User safety in view of the dosing systems, i.e. the automatic dosing system is to be designed such in combination with the product containers that the users are protected from contact with the product.
4. Stable, long-lasting implementation for an optimally long service life, i.e. a higher number of refillings. Labeling impressed insofar as possible, milled or applied non-erasably in some other way so that reliable sorting according to type of product can be implemented before refilling-without additional labeling.
5. Container and closure material identical with good, environmental disposal possibility in the ultimate disposal.

All thermoplastic plastics from which the described packing elements can be manufactured with suitable, known production methods (for example, blowing but, in particular and particularly preferred, injection molding) come into consideration as materials for the containers as well as for the container covers.

A prerequisite is that the plastics employed in the described embodiment of the packing comprise adequate shape stability, even given occasional application of impact loads or compressive forces, temperatures between approximately 0° C. and 85° C. (when being washed), ultraviolet rays (due to natural or artificial light). A further prerequisite is that the plastics employed are compatible with the chemicals contained as filled product (particularly detergents, cleaning agents, rinses, detergents, disinfectants, water-treatment agents), even at higher temperatures up to approximately 85° C. as well as prolonged influencing times.

It is desirable that the plastics employed can either be supplied for reemployment (production of plastic granules) or to an unproblematical, thermal utilization (burning) after the expiration of the multiple-use time. For this reason, halogen-free, particularly chlorine-free plastics are to be preferably employed.

Polyethylene and polypropylene, particularly high-pressure PE or, respectively, PP are therefore especially preferred.

DE-A-28 51 605 is directed to a stackable cover or, respectively, floor for a container. The cover or, respectively, floor is constructed such that it comprises a let-in double wall and a circumferential edge in which a channel for mating acceptance of the cover or, respectively, floor edge of the container is shaped.

WO-A-92/12062 discloses stackable, returnable containers for hazardous materials. The container covers comprise no grip.

SUMMARY OF THE INVENTION

It is therefore the object of the present invention to develop a method for manufacturing pressed, molded and at least partially porously fashioned blocks of detergent, cleaning agent, disinfectant and/or preservative without having to incorporate a strong pressing process and without having to melt or dissolve a raw materials mix or parts thereof with thermal energy before being filled into a mold, whereby a compact block nonetheless arises wherein the powder structure is still recognizable or, respectively, that is at least partially porously fashioned.

Further, new recyclable, upwardly open as well as conically upwardly expanding returnable containers should be made available, whereby all parts of these containers should be capable of being simply and easily rinsed (manually and by machine). These new returnable containers should be employable for liquid, solid or, respectively, powdered detergent, cleaning agent, disinfectant and/or preservative and should particularly be employable for the implementation of the afore-mentioned method. Further, a recyclable returnable container, particularly one containing detergent, cleaning agent, disinfectant and/or preservative suitable for employment in dishwashers and washing machines, should be made available that is fashioned such that detergent, cleaning agent, disinfectant and/or preservative is delivered from this container when a stream of aqueous liquid is discharged onto a surface of the detergent, cleaning agent, disinfectant and/or preservative exposed to said stream of aqueous liquid. Further, this container containing cleaning agent should be capable of being introduced into a dosing device for dissolving this agent that is adapted to this container.

These objects are achieved by the characterizing parts of claims 1, 2 or, respectively, 18, 26 or, respectively, 28, 29 as well as 30.

Advantageous developments of the invention are contained in the subclaims.

DETAILED DESCRIPTION OF THE INVENTION

Figure 1:
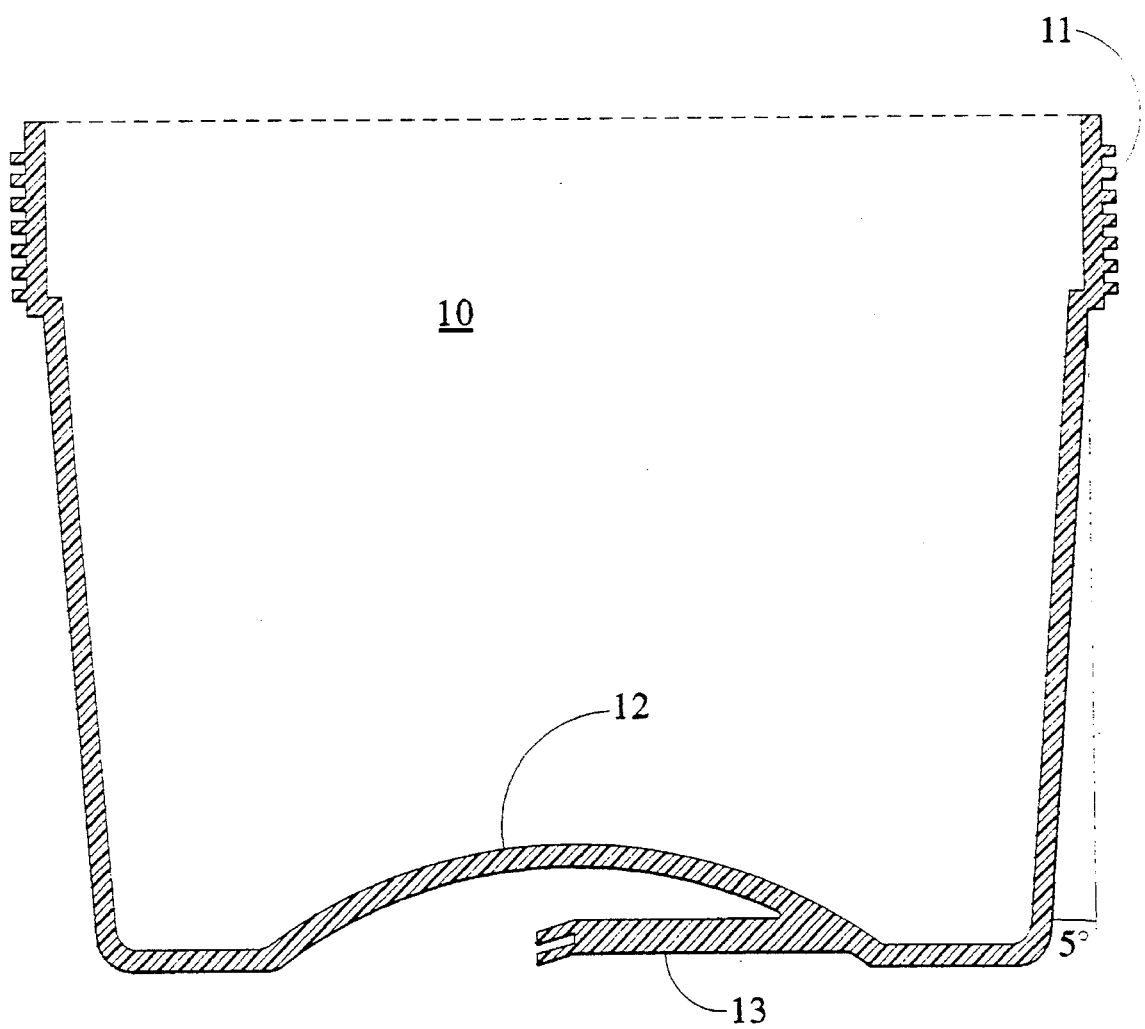
FIG. 1 shows a cross section through an empty product container (2.5 liters) of the invention composed of 2 mm thick polyethylene (HP) that is manufactured as an injection molded part and into which powder granules can be filled.
Figure 2:
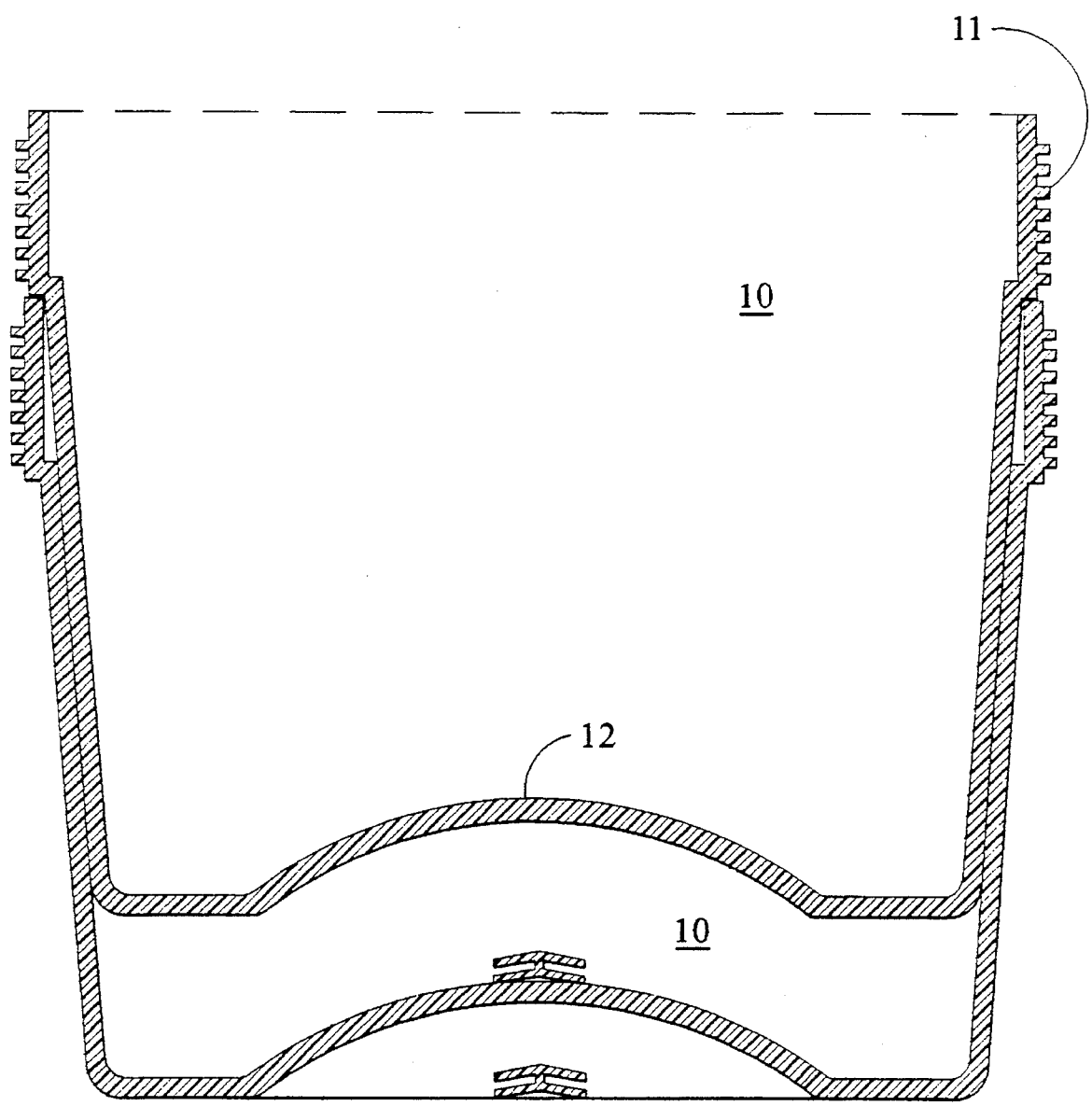
FIG. 2 shows a cross section through two containers (2.5 liters) of the invention stacked inside one another.
Figure 3:
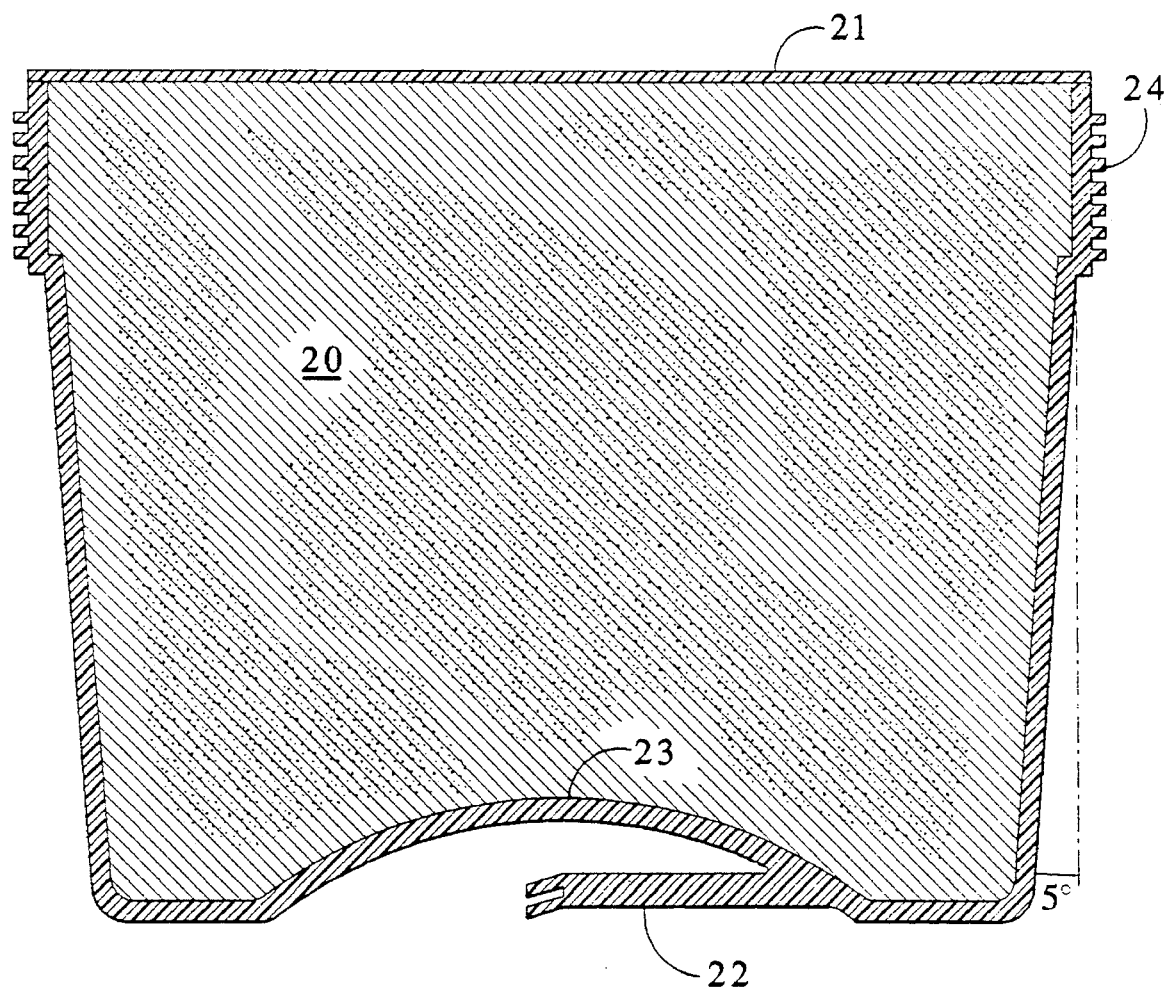
FIG. 3 shows a cross section of a container of the invention filled to the brim with detergent, cleaning agent, disinfectant and/or preservative, said container being closed with a foil (for example, PVA or PE retainer foil).

It has been found that a solidified, compact block of detergent, cleaning agent, disinfectant and/or preservative that, however, was not cast in molten form and wherein the powder structure is still recognizable can be surprisingly manufactured when a prefabricated premix composed of powdered and/or granulated active ingredients and process materials is mixed with a suitable, water-soluble binder that is liquid at the manufacturing temperature in a suitable mixing device, preferably in a flow-through mixer, so that a moistened but still pourable powder mass arises, so that this powder mass, potentially without previous addition of binder as well, is compressed upon application of pressure- but without pressing greatly—, so that a compact block wherein the powder is still recognizable arises due to the following solidification. The afore-mentioned addition of binder is not obligatory in every case since the active ingredients utilized contain constituent water that can be adequate in order to allow a moistened but still pourable powder mass to arise.

An especially preferred embodiment of the method of the invention is composed therein that a prefabricated premix of powdered and/or granulated substances (active ingredients) is mixed in an amount between 1 and 29 mass percent with a suitable water-soluble binder that is liquid at the manufacturing temperature, being mixed therewith in a suitable mixing device, preferably in a flow-through mixer, so that a "moistened" but still pourable powder mass arises; that the latter is filled into the container and is compressed (but not greatly pressed) upon application of pressure, particularly $1 \times 10^4$ through $1 \times 10^6$ pa (0.1–10 atmospheres) with a pressure die having the desired surface fashioning (planar or dome shaped), whereby a compact block wherein the powder structure is still recognizable (but which is not cast in molten form) arises due to following solidification. This block can be additionally "sealed" with an infused solution or melt of a water-soluble substance, so that a closed, smooth surface arises. By contrast to the mass set forth later, this sealing layer need not exhibit its own mechanical strength; rather it serves more of a purpose of optical design and potentially serves as protection against harmful attacks on the skin if the surface is touched.

The described binder can be water, an aqueous solution or dispersion of one or more water soluble salts or of an organic substance or can also be a heated, free-flowing melt or a gel. The binder itself can but need not necessarily be crystalizable itself at temperatures between 0° and 40° C. The binder is utilized in parts of 1–29 mass percent, preferably 2–10 mass percent and, especially preferred, 3–8 mass percent with reference to the finished, overall mixture.

The binder itself can but need not contain constituents having an active cleaning effect. A 30–60% by weight aqueous solution of alkali (ortho, pyro, or poly-) phosphates is especially suitable.

The described sealing layer can be achieved with a casting compound that comprises a composition identical to or different from that of the binder. By contrast to the binder, however, this casting compound must be solid or at least gelatinous at temperatures between 0° and 40° C. The proportion of casting compound referred to the overall fill content lies between zero (when sealing is forgone) and a maximum of 20%.

A polyethylene glycol that is solid at 0°–40° C. or a derivative thereof terminated by an end group or a crystalizable solution or melt of one or more salts such as soda, sodium sulfate, alkali polyphosphate that solidifies at 0°–40° C. or acids such as citric acid or mixtures of these constituents can preferably be employed as casting compound for manufacturing a retainer layer.

In particular, a mixture of 30–50 mass percent water as well as 20–50 mass percent sodium polyphosphate and/or 20–50 mass percent soda and/or 20–50 mass percent sodium sulphate can be utilized as sealing layer, whereby either only one salt or a combination of two or three suitable salts is contained therein and the solids content lies between .50 and 70 mass percent. In an especially preferred embodiment, the sealing layer can be composed of a mixture of 50 mass percent water, 25 mass percent sodium polyphosphate and 25 mass percent soda.

The raw materials that are usually offered for the detergent, cleaning agent, disinfectant and preservative are present in powdered or granulated form. The individual particles of the active ingredients and adjuvants or the detergent have a preferred diameter between 0.01 and 3 mm.

The particle size of the constituents employed for the outer mixture is not especially critical.

Particularly given constituents that can be delivered in technical quality in usable grain sized, for example approximately 0.05 through approximately 1.0 mm, such grain sizes will be directly employed. The employment of powders having many fine parts, i.e. below one tenth or a few tenths of a millimeter, is not disadvantageous in the present process.

The blocks manufactured with the method of the invention and solidified in the container can be employed for washing, cleaning, rinsing as well as for disinfecting or, respectively, for antimicrobial treatment or, respectively, for deodorizing treatment of water circulations and water-carrying systems.

DESCRIPTION OF THE PREFERRED EMBODIMENT

The method of the invention shall now be set forth in greater detail on the basis of the following examples.

EXAMPLE 1 a) Powder premixes having the following composition were produced in a batch mixer (respectively in percent by weight):

|  | A | B | C | D |
|---|---|---|---|---|
| Sodium Tripolyphosphate | 44 | 29 | 55 | 10 |
| Sodium Hydroxide Beads | 40 | — | 18 | — |
| Soda (Powder) | 12 | 15 | — | 85 |
| Sodium Dichloroisocyanurate.2H$_2$O | 3 | 5 | 2 | — |
| Sodium Metasilicate (anhydrous) | — | 50 | 25 | — |
| Non-ionic Surfactant (Lutensol ® LF 131) | 1 | 1 | — | 5. | b) A binder mix composed of 50% water and 50% sodium polyphosphate was produced and brought to a temperature of 20° C.

c) Respectively 92 mass percent of the respective powder mixture A–D were initially mixed with 8 mass percent each, whereby an increase in the temperature was already observed during mixing, this having then subsequently risen to 65°–70° C. The resulting, moist but pourable powder masses were introduced into the containers 20; 30; 40; 50 (see FIGS. 1–5) up to the brim (2.5 liters) and were compressed upon application of slight pressure with a smooth die having a planar surface. The containers were then closed with a screw-on cover and were stored at room temperatures (20°–25° C.). A check after six hours showed that a compact mass had arisen in the containers.

The containers were capable of being introduced with their opening downward into the wash-in means 80 (see FIG. 12) provided with a strainer insert 81 without powdered or granulated constituents crumbling and falling out. The entire contents of the container could be unproblematically removed by spraying with water from a nozzle 84 under the strainer 81. After the end of rinsing phase, the emptied packs contained no visible residues whatsoever.

EXAMPLE 2

The same mixtures as described under 1 a) through c) were manufactured and filled into the containers in a second series of trials. After compression with the die, respectively 100 ml of a thin-bodied mixture of 40 mass percent water, 40 mass percent sodium polyphosphate and 20 mass percent soda heated to 60° C. was respectively infused and this mixture then uniformly distributed itself on its own. The containers were screwed shut and left standing at room temperatures. The covers were removed and the filled masses were checked after a waiting time of six hours. As set forth under 1, a pressure-resistant mass which, however, exhibited a uniformly smooth, closed, solid surface also occurred here. These containers could also be unproblematically introduced into the wash-in means 80 with their opening pointing down and could be rinsed residue-free by being sprayed with water.

EXAMPLE 3

The following powder mixture was manufactured in a third series of trials:

| | |
|---|---|
| sodium hydrogen sulfate powder | 60% by weight |
| citric acid monohydrate powder | 10% by weight |
| sodium sulfate (anhydrous) powder | 29.8% by weight |
| non-ionic surfactant (powder) (stearic acid alcohol having 25 mol ethylene oxide) | 0.1% by weight |
| lemon fragrance | 0.1% by weight |

This mixture was then treated as set forth in greater detail in examples 1 b and 1 c, was filled into the containers and, after being compressed with the die, the powder block was sealed in a compound as set forth in example 2.

The containers were screwed shut and left standing at room temperature. The covers were removed and the filled compounds were checked after a waiting time of six hours. As set forth under 1, a compression-proof mass which, however, exhibited a uniformly smooth, closed, solid surface also occurred here. These containers could also be unproblematically introduced into the wash-in means 80 with their opening pointing down and were capable of being rinsed residue-free by being sprayed with water.

Recyclable, upwardly open as well as conically expanding returnable containers for liquid, solid or, respectively, powdered detergent, cleaning agent, disinfectant and/or preservative are another subject matter of the invention, these being particularly suitable for the implementation of the above-described method of the invention. The returnable containers of the invention are fashioned open and both without undercuts as well as rounded, so that all parts can be simply and easily rinsed out (manually and by machine). All containers can be stacked inside one another in a space-saving way. The product containers of the invention are provided with a stacking slope or 2°–7°, particularly with a stacking slope of 5° or, respectively, 3.3°, and are fully opened toward the filling and dosing opening.

In preferred embodiments, the stacking slope amounts to 3.3° for 5 liter containers and amounts to 5° for 2.5 liter containers.

A stable outside thread for the purpose of being screwed to what is likewise a solid screw-on cover that, for example, can be fabricated of 2 mm polyethylene (HP) and of a seal is located at the open side. The floor of the container is equipped with a depression and contains a grip projecting into this depression for manipulating and transporting the container. In one embodiment, the depression can be dome shaped; this, however, does not limit the invention to this embodiment.

Both the filled and closed container as well as the empty container and the cover is (are) stackably fashioned in and of itself (themselves).

All thermal plastic plastics that can be manufactured by blowing, particularly by injection molding, come into consideration as materials for the containers of the invention. Materials such as polyethylene, polypropylene and, in particular, high-pressure polyethylene or, respectively, polypropylene are preferred. The plastics for the containers of the invention must be selected such that the containers exhibit adequate shape stability even given the occasional application of impact or pressure forces, temperatures between approximately 0° C. and 85° C., ultraviolet rays. Further, the plastics for the containers must be compatible with the chemicals to be filled thereinto, particularly detergents, cleaning agents, rinsing agents, detergents [sic], disinfectants as well as water treatment agents, even given higher temperatures up to 85° C. as well as prolonged influencing times. Multi-layer returnable containers that, for example, are manufactured of a polyamide outside or inside layer and of a barrier layer lying therebetween can therefore also be utilized. After expiration of the multiple use time, the plastics of the containers of the invention can be supplied for reemployment, i.e. a production of plastic granules or for unproblematical thermal utilization, i.e. burning. For this reason, no plastics such as polyvinyl chloride should be employed; rather, only halogen-free, particularly chlorine-free plastics should preferably be employed.

Figure 12:
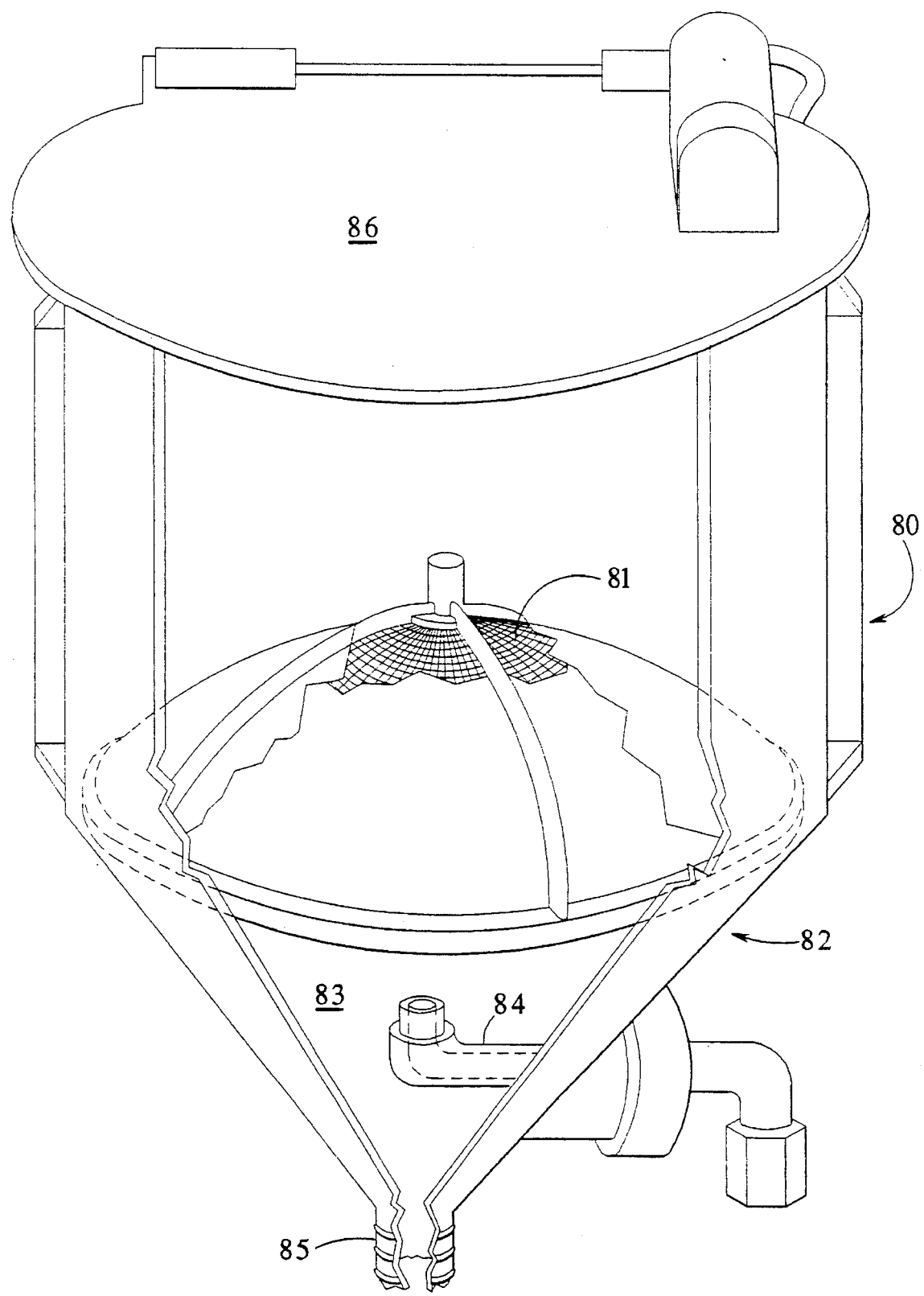
FIG. 12 shows a dosing device for dissolving detergent, cleaning agent, disinfectant and/or preservative.
Figure 13:
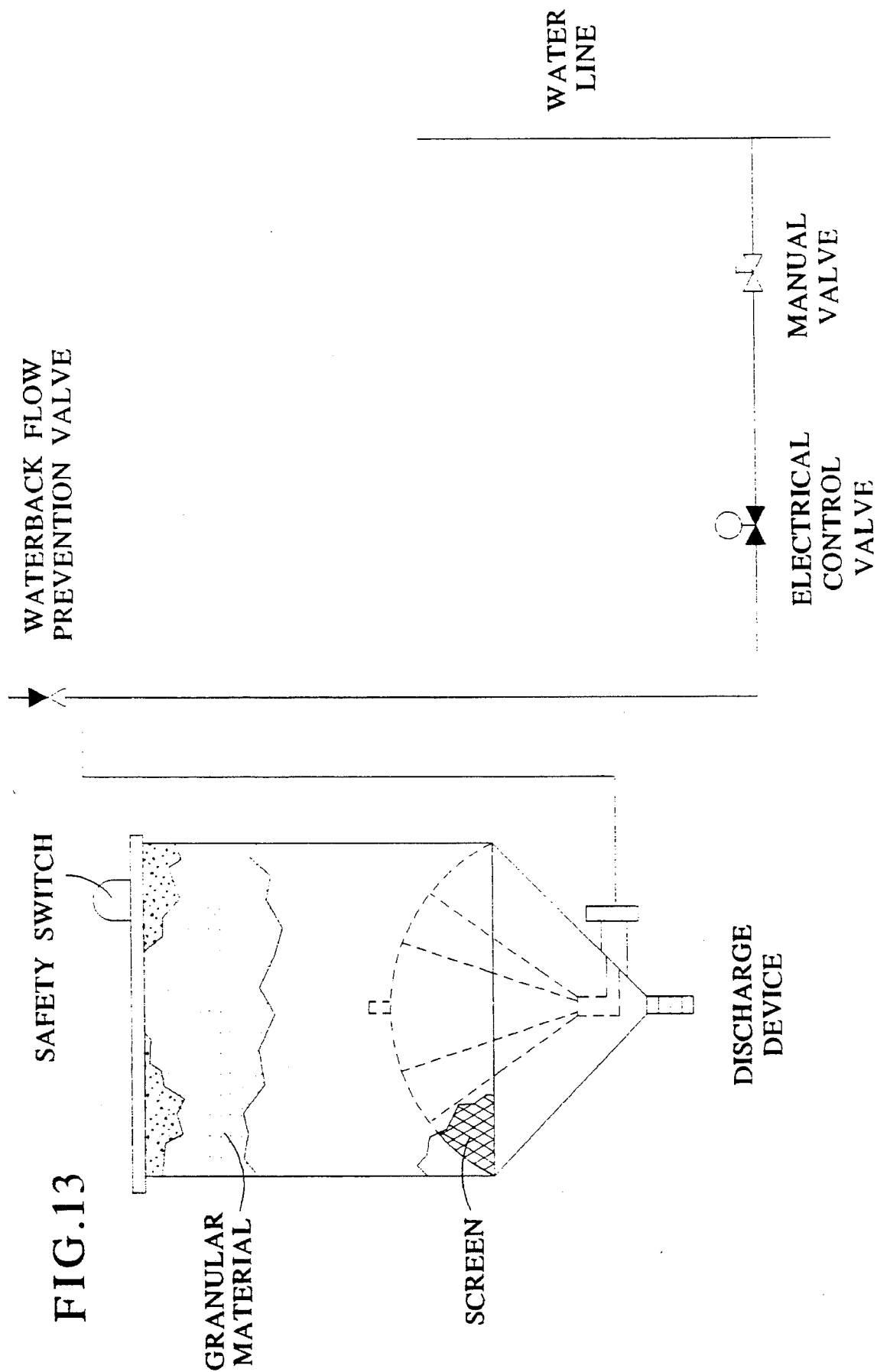
FIG. 13 schematically shows the dosing device of FIG. 12 that is connected to a water conduit via intervening valves.
Figure 14A:
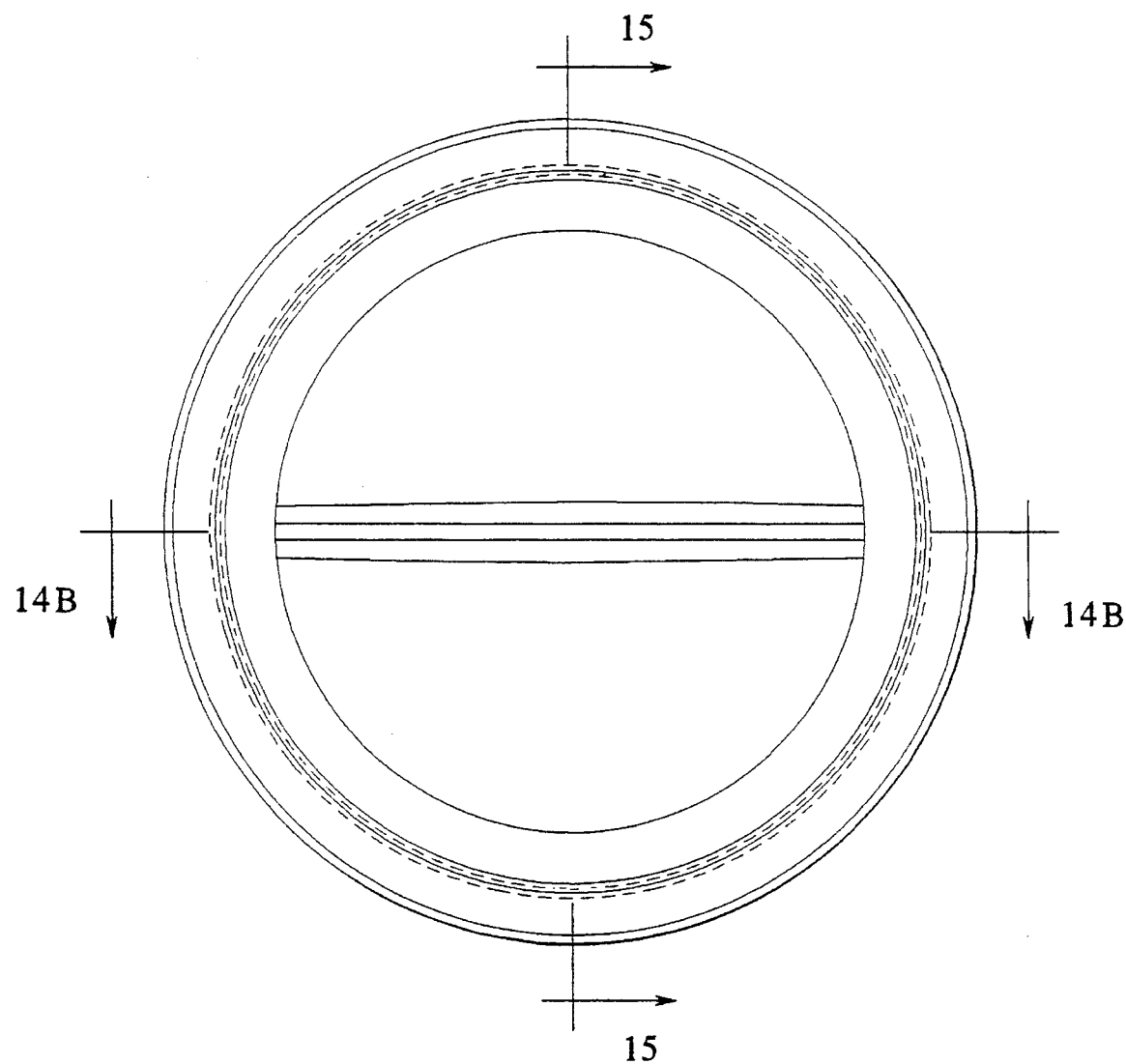
FIG. 14 shows another embodiment of a recessed cover that can potentially be fashioned dome-shaped.
Figure 14B:
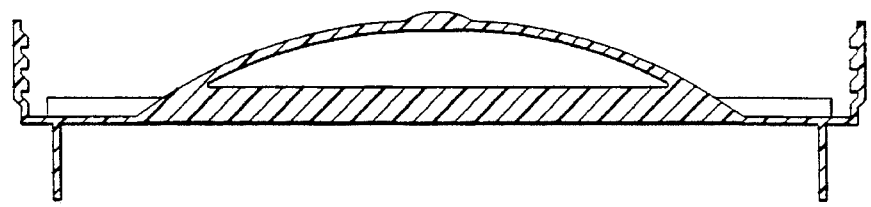
Figure 15:
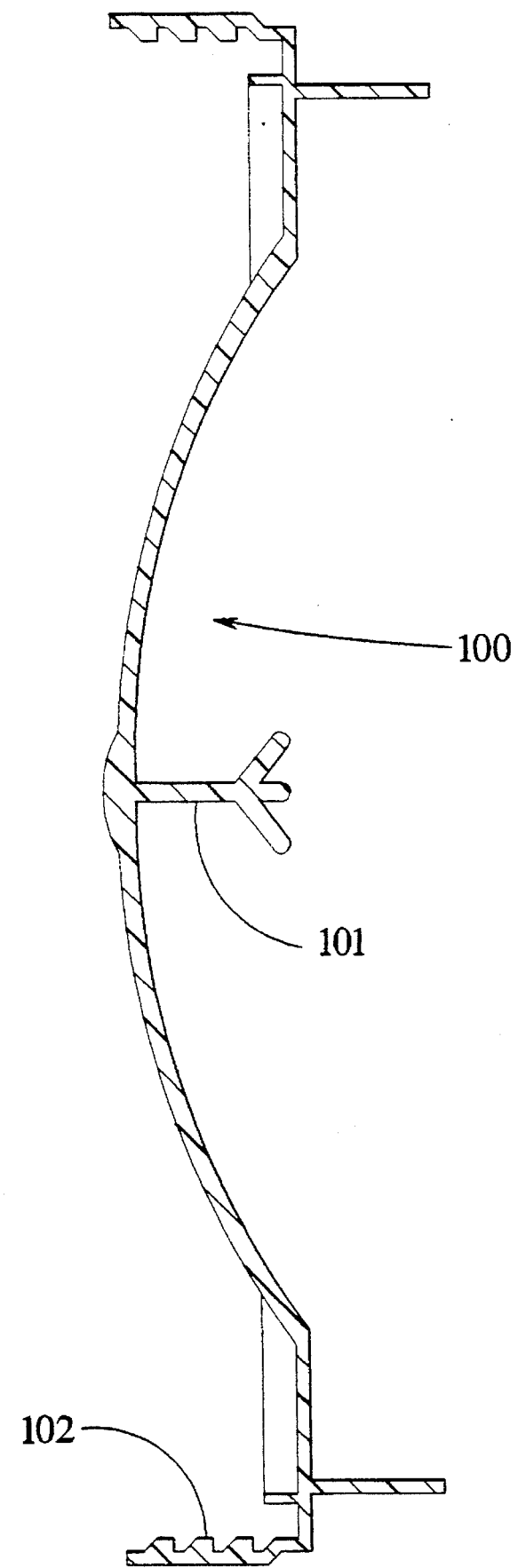
FIG. 15 likewise shows another embodiment of a recessed, particularly dome-shaped cover with grip.

The recyclable returnable containers of the invention as well as the covers thereof are shown in FIGS. 1–11 as well as 14 and 15. The dosing device is shown in FIGS. 12 and 13.

The recyclable containers 10; 20; 30; 40; 60 of the invention shown in FIGS. 1–5 as well as 8 and 9 are upwardly open and expand conically in upward direction. They are intended for liquid, solid or, respectively, powdered detergent, cleaning agent, disinfectant and/or preservative. The containers 10; 20; 30; 40; 60 are manufactured as an injection molded part of 2 mm thick polyethylene (HP) and have been provided with a stacking slant of 5°. They are completely opened without undercuts toward the filling and dosing opening. A stable outside thread 11; 24; 34; 44; 63 for the purpose of screwing with a likewise solid screw-on cover 50; 70; 90; 100 is located at the open side. The cover 100 and the floor 23; 42; 61 of the product container are fashioned with a stable grip 13; 22; 32; 43; 62, so that the product container 10; 20; 30; 40; 60 can be simply manipulated, transported and opened. Simultaneously, a solid closure 50; 70; 90; 100 (see FIG. 6, FIG. 11) is provided for safe storage and transport.

In a specific embodiment of the covers 50; 70; 90; 100, these can be equipped with a specifically attached, smaller cover (for example, cover 71). Normally, however, no smaller covers or the like are applied in the coverings of the invention.

Figure 4:
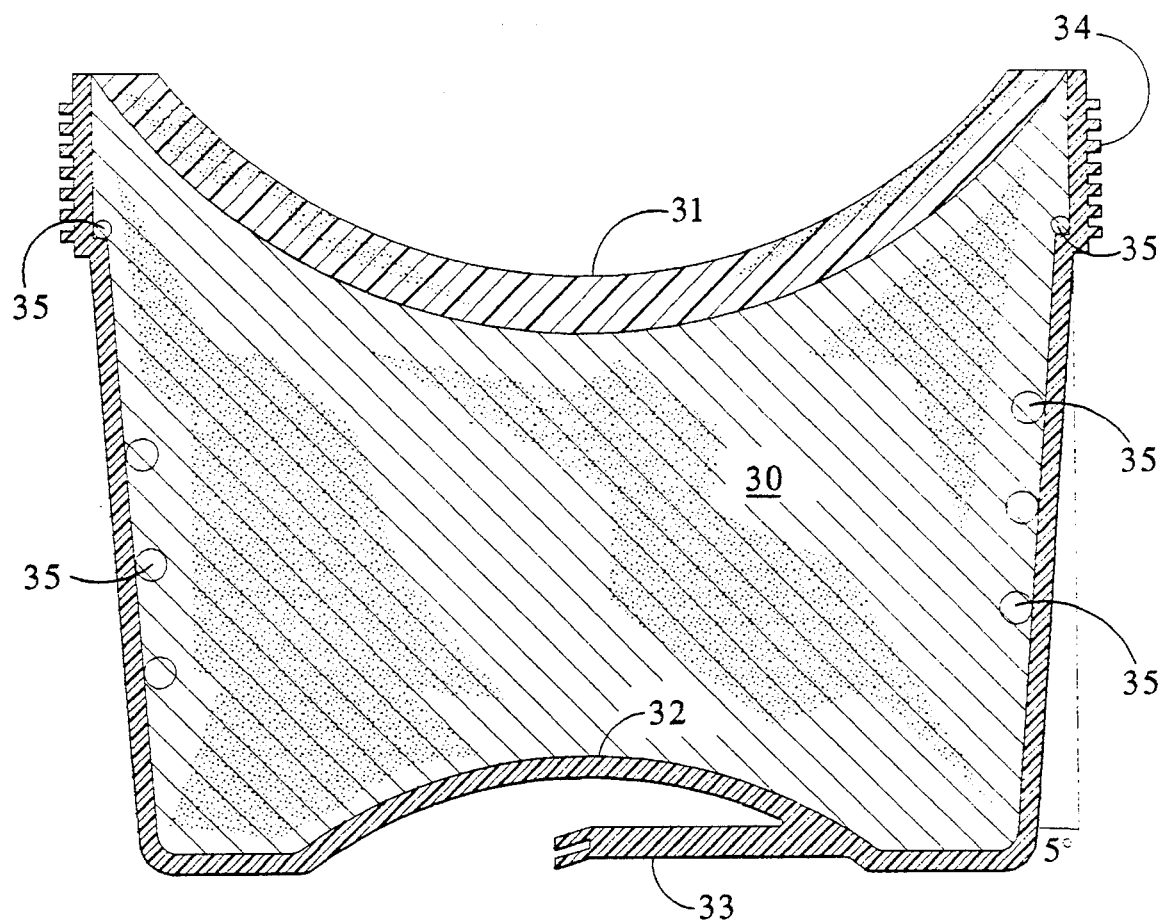
FIG. 4 shows a cross section through a container of the invention that is filled to the brim with detergent, cleaning agent, disinfectant, and/or preservative (with or without a binder additive) and onto which a retainer layer has been fused.
Figure 5:
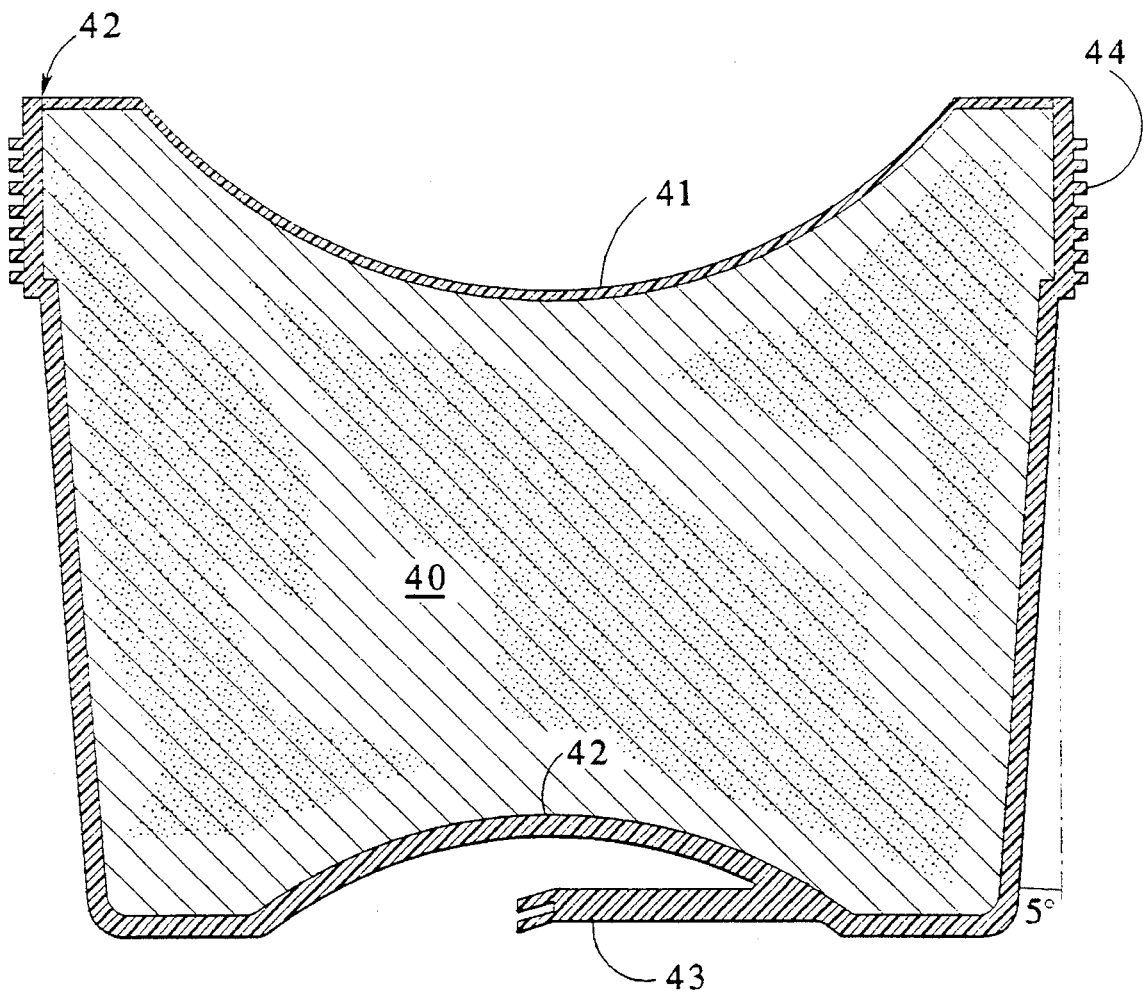
FIG. 5 shows a cross section through a returnable container of the invention into which the detergent, cleaning agent, disinfectant and/or preservative product has been filled (without binder additive) and onto which a water soluble PVA preform has been applied and that has been subsequently compressed with a dome-shaped press.
Figure 6:
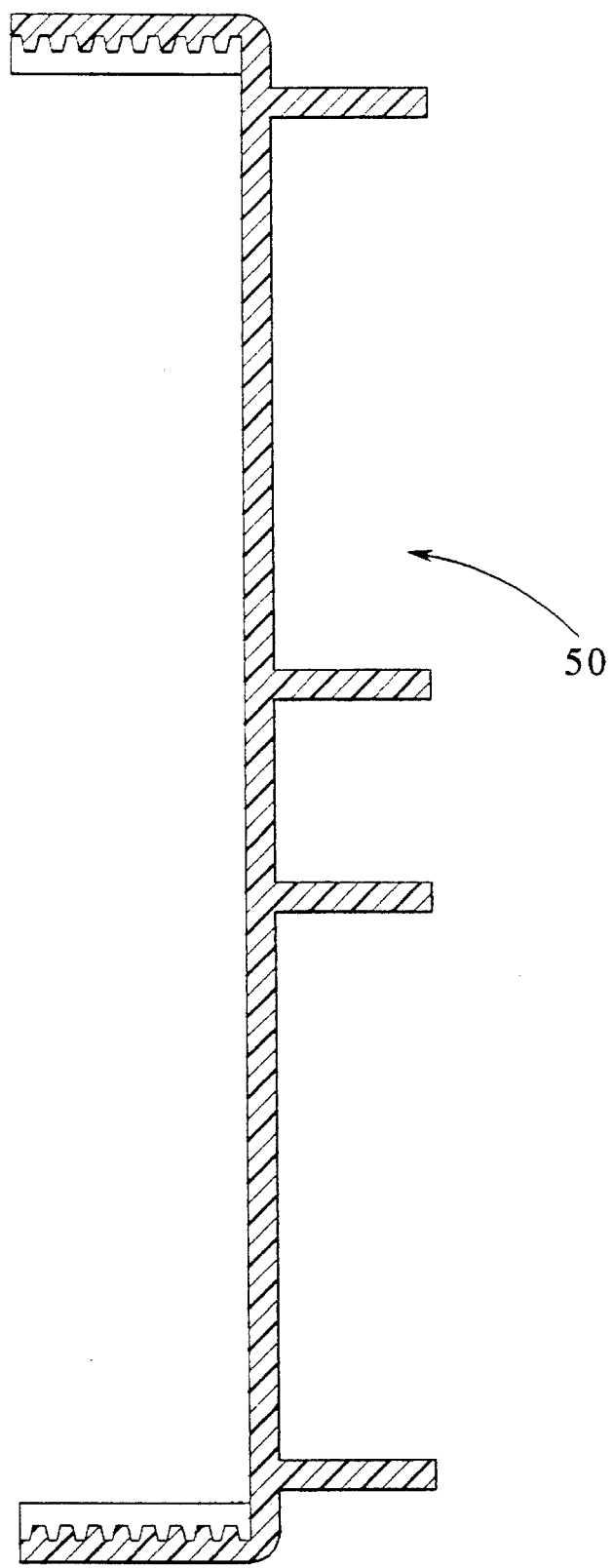
FIG. 6 shows a cross section through a covering of polyethylene of the invention for a returnable container of the invention.
Figure 7:
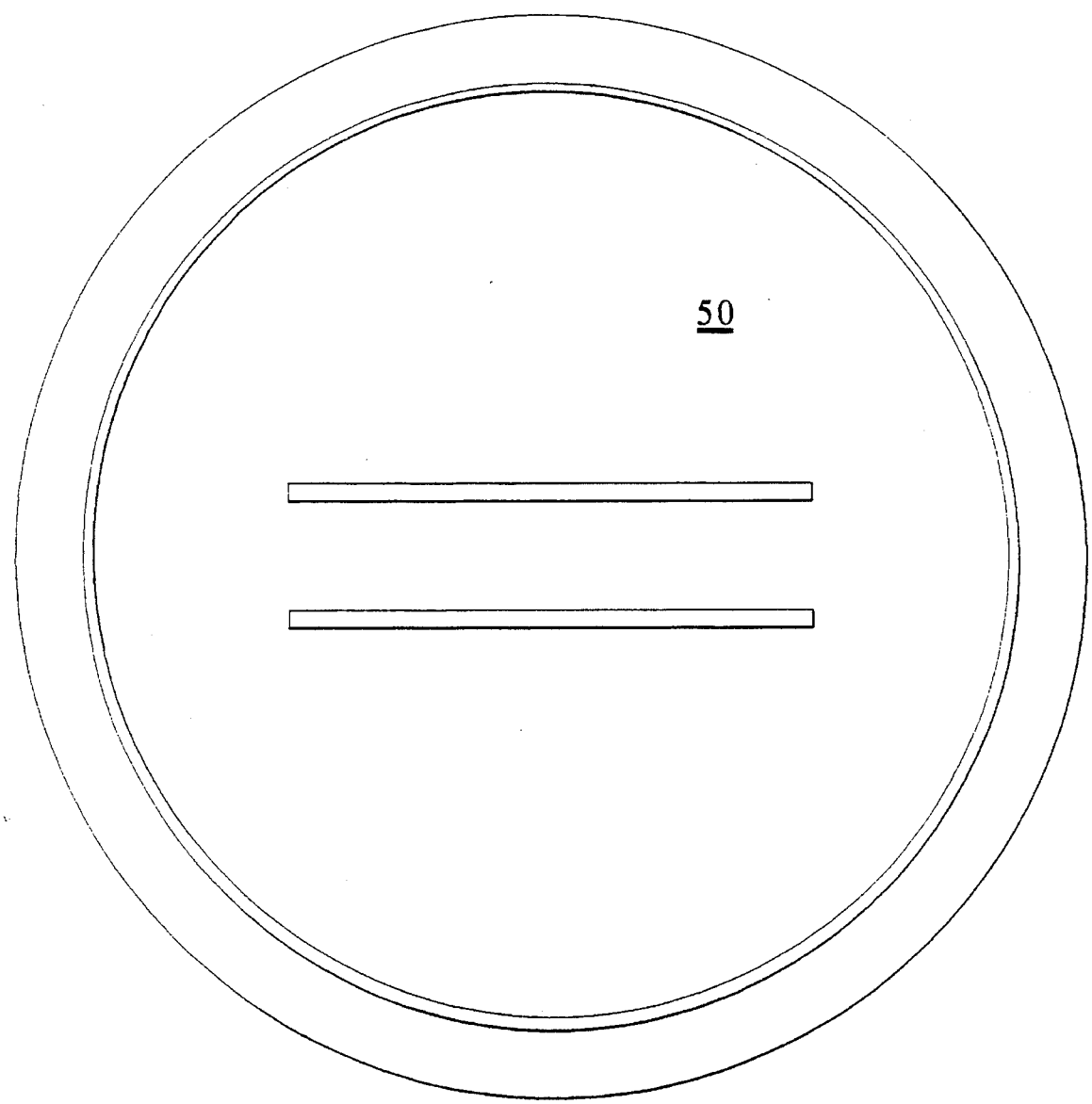
FIG. 7 shows a plan view onto a cover according to FIG. 6.
Figure 8:
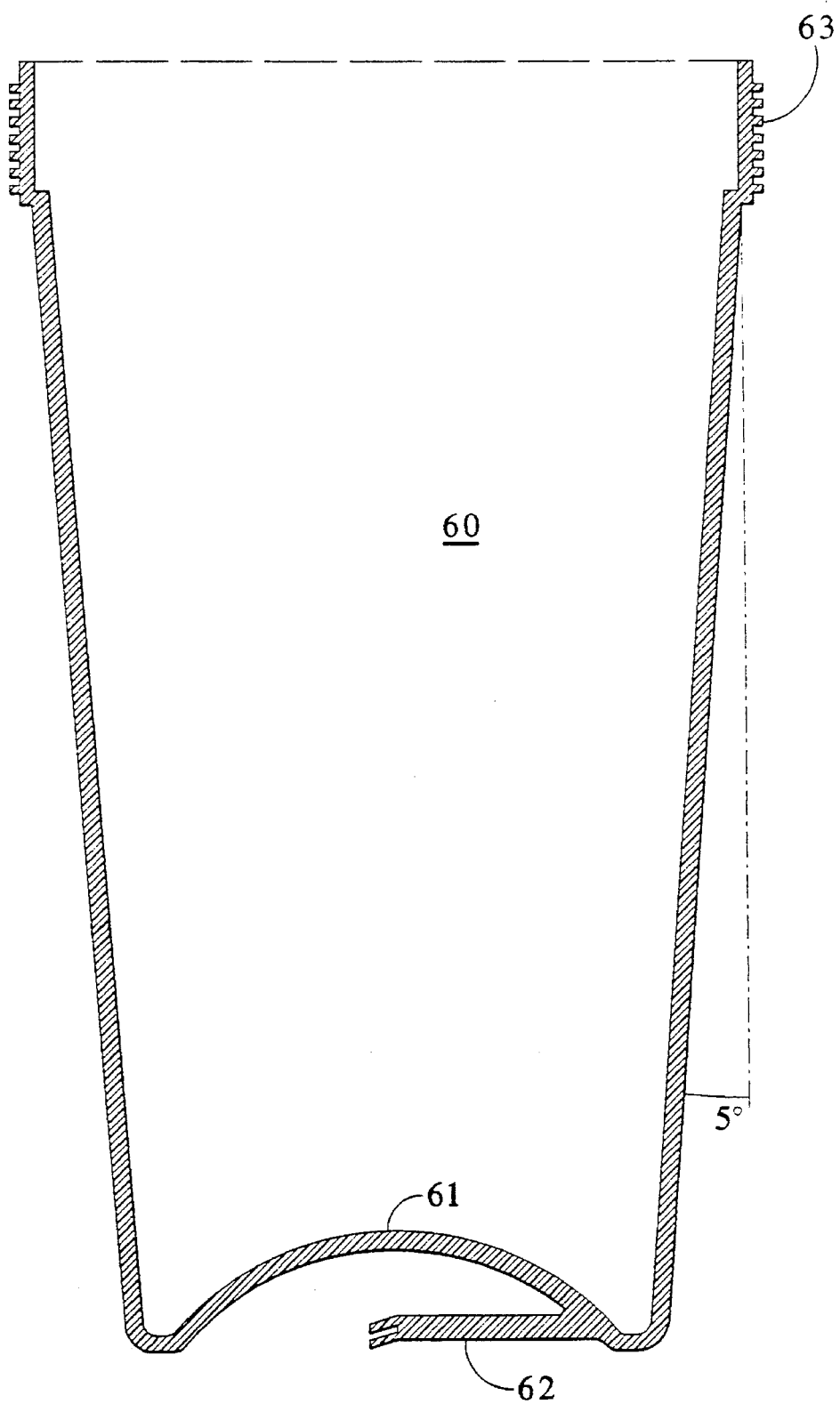
FIG. 8 shows a cross section through a product container (5 liter) of the invention for liquid products and powder granules.
Figure 9:
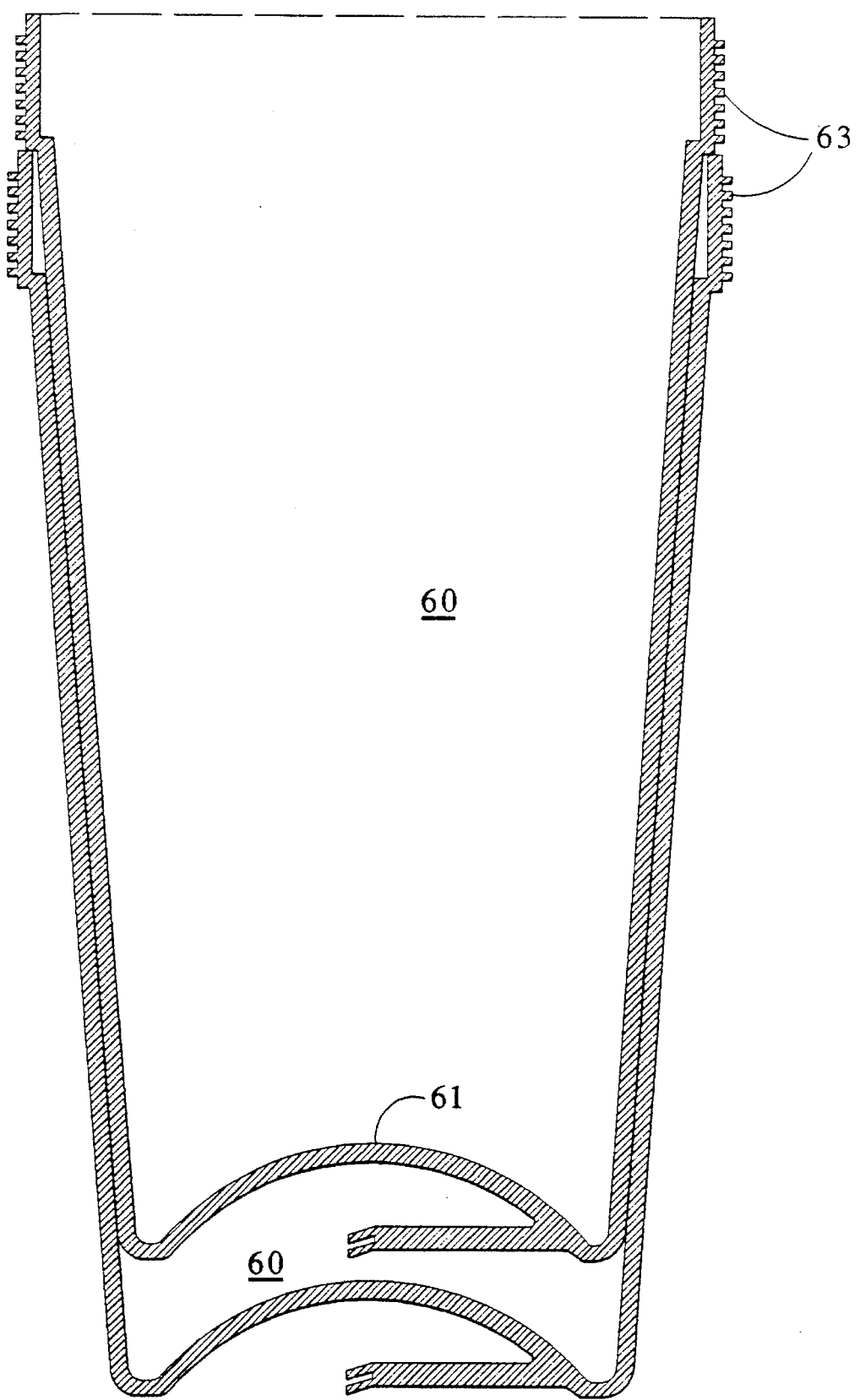
FIG. 9 shows a cross section through two containers (5 liter) of the invention according to FIG. 8 stacked inside one another.
Figure 10:
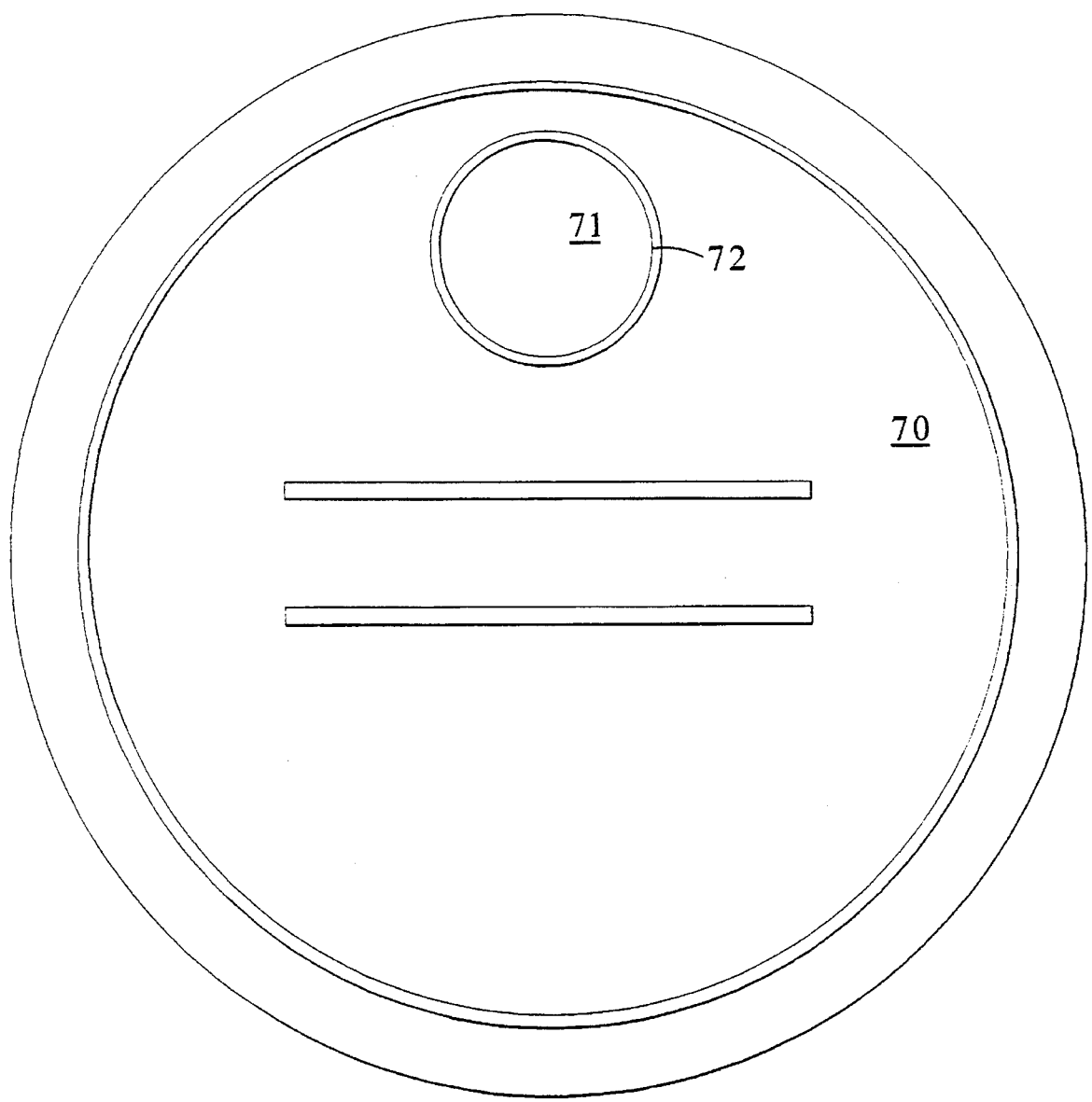
FIG. 10 shows a plan view onto a specific embodiment of a cover of the invention which comprises a smaller cover as well as an acceptable thread therefor.
Figure 11:
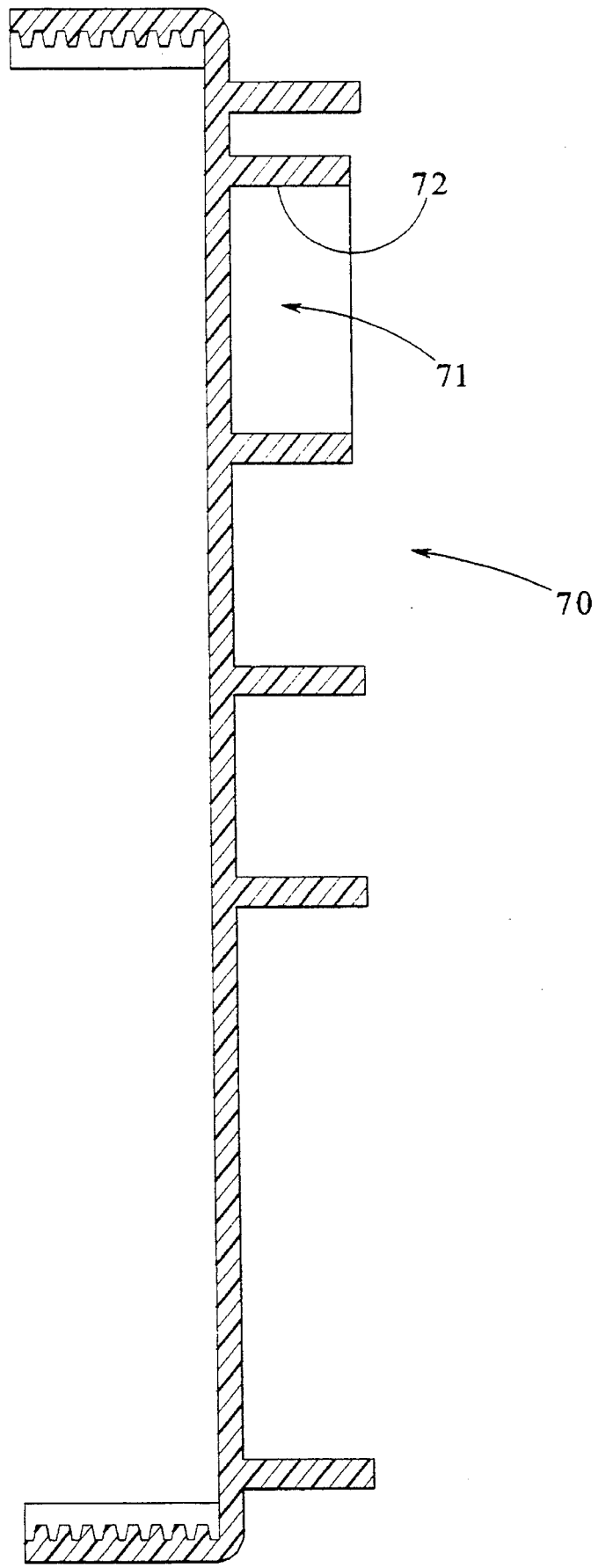
FIG. 11 shows a cross section through the cover of FIG. 10.

In a further, special embodiment, one or more holders 35 can be attached to the inside of the container wall (see FIG. 4).

The required quantities of liquid contents can be poured from the containers of the invention in a traditional way, potentially with the assistance of discharge aids or faucets, or, on the other hand, can be suctioned or dosed from the packs with the assistance of pumps and suction lances in conformity with a controlled metering control.

A specifically attached, small cover 71 (see FIG. 10 and FIG. 11) is opened and a commercially obtainable suction lance for a suction jet device is introduced. The dosing (suctioning) continues until the product container is completely emptied. After this, the suction lance can be in turn removed and introduced into another, filled product container. The large screw-on cover 70 is now screwed off.

Powdered or granulated contents can either be removed from the container of the invention in a traditional way or, insofar as the surface is terminated in a suitable way during filling in order to prevent trickling, on the other hand, can be dissolved and dosed into the system with a controlled, pulsating washing of the granule surface 82 by having the container opening placed downward into a wash-in means 80 equipped with a strainer insert 81 (see FIG. 13).

The following can thereby serve as closure principle for preventing trickling wherein the container 20; 30; 40 and placement into the dosing device 80 with the opening in downward direction:

a) filling the container 20; 30; 40 and terminating closure with a non-water-soluble foil that, for example, can be closed with a PE retainer foil 21 (see FIG. 3) which is slit open in the wash-in means 80, so that only then can the contents trickle out in the wash-in means 80.

b) the container 40 is closed with a water-soluble foil 41 that is applied over the container opening by hot-sealing, gluing, mechanical fastening and that is supported by the screwed-on screw-type cover during transport. When introduced into a dosing means 80 with the opening in downward direction and when the foil 41 is rinsed with water, potentially while being heated, this foil 41 dissolves in a short time, so that the powdered or granulated contents can trickle onto the strainer insert 81.

c) the container 30 is filled with the detergent with and without binder. In an embodiment according to FIG. 4, the container contents is shaped and potentially compressed with a dome-shaped pressure die; in another embodiment which is not illustrated here with a separate drawing, a planar surface can also be produced. Subsequently, a retainer layer composed of a water-soluble compound is applied. This mass can also be composed [of] a high-viscosity, heated melt, a preferably high-viscosity, solidifiable solution or of a solidifiable powdered substance.

In another embodiment, the product with or without binder additive is filled into the container and a water-soluble PVA preform 41 is applied with subsequent pressing by a dome-shaped press. Additional interlocking holding points 42 can also be applied to the product container 40 (see FIG. 5).

This afore-mentioned coating of the powder in the container 20; 30; 40 with a water soluble compound that is solid at temperatures between approximately 0° C. and approximately 40° C. occurs in such a way that a layer firmly pressing against and adhering to the container wall is formed with a suitable thickness (of, for example, 1–2 cm), this preventing the contents from trickling out when the container is inverted and introduced into the wash-in means 80. With respect to its chemical composition, of course, this compound must be compatible with the filled contents. Dependent on the filled contents, for example, this can be a matter of a polyethylene glycol that is solid at 0°–40° C. or a matter of a derivative thereof terminated with an end group or can be a matter of a crystalizable solution or melt of one or more salts such as soda, sodium sulphate, alkali polyphosphate or, respectively, of a solution or melt of one or more salts such as soda, sodium sulphate, alkali polyphosphate that solidifies at 0°–40° C. or also can be a matter of acids such as citric acid. This "layer-forming" substance is preferably selected such that, given potentially accidental contact with the skin when manipulating the container, this contact does not produce any negative consequences on the skin such as irritation, caustic burning.

As shown in FIG. 12, the dosing device 80 for dissolving detergent, cleaning agent, disinfectant and/or preservative is composed of a firmly closable container 81 having a dosing strainer 81 resting on a base 82, this dosing strainer 81 being intended for receiving the substances to be dissolved that are situated in a product container 20; 30; 40, of a sprayer 84 attached in the container discharge part 83 concentrically under the strainer 81, and of a discharge nozzle 85 attached concentrically in the discharge part 83. The filling of the dosing means is implemented in the following way. The respective screw-on cover is removed by being screwed on [sic] from the respective product container 20; 30; 40. The rinsing agent or detergent contained therein cannot trickle out due to the attached retainer foil or, respectively, retainer layer or due to the retainer preform; rather, they remain tight and protected in the container. With its opening directed down, the product container 20; 30; 40 is introduced into a dimensionally adapted, specific dosing device 80 and is put in place thereat on a dosing strainer 81 (see FIG. 12, FIG. 13). The dosing strainer 81 can comprise the greatest variety of shapes. It is dome-shaped in one embodiment. The cover 86 of the dosing device 80 is closed. Given a requested dosing as a result of being rendered conductive, the water-soluble retainer elements (foil, retainer layer or retainer preform) are then dissolved in the dosing device 80 and the powder granule is then dissolved by being sprayed with an aqueous liquid from the sprayer 84. The dosing device 80 can be controlled with continuous variation, so that powder granule is delivered from the product container 20; 30; 40 until cleaning agent or, respectively, detergent is no longer present therein. After this, the control device sounds an alarm (optically and acoustically) and the operating personnel takes the empty product container out and introduces an open, filled, new product container.

We claim:

1. An environmentally sound product containing dispenser package comprising:

a product container including a unitary molded stackable container body having a closed bottom end, an opposed end, a releasable cover member for selectively closing the open end of the container body, an external thread connecting said container with said cover, and an upwardly and outwardly angled upstanding peripheral side wall having a stacking angle of from about 2° to about 7° extending between the bottom end and the open end, said container body defining a smooth, rounded, frusto-conical product receiving cavity having no undercut portions, said closed bottom end further including an inwardly and upwardly directed domed-shaped region therein including a handle grip portion defined in an outwardly facing side of the domed-shaped region opposite the product receiving cavity;

a known quantity of product disposed in the product receiving cavity, said product being a shaped block of a pre-moistened, compacted, finely-divided powder comprising an agent selected from the group consisting of detergents, cleaning agents, disinfectants, preservatives and mixtures of any of the foregoing, compacted under application pressures of between about $1 \times 10^4$ to about $1 \times 10^6$ Pa to provide a shaped block wherein powder structure is still recognizable; and means for maintaining the product in the cavity in an open topped condition even upon inversion of the container body so that the open end faces downwardly, whereby the product dispenser package may be opened, inverted and loaded into a flushing chamber of a product dispenser apparatus without spilling and wasting the product and without causing human contact with the product, said product being fully removable on flushing contact with a flushing media sprayed into said open end to provide a residue free reusable, recyclable container.

2. A product dispenser package as defined in claim 1, wherein the product container comprises a unitary molded thermoplastic container body molded from a high grade dimensionally stable, UV-resistant and chemical resistant thermoplastic molding composition.

3. A product dispenser package as defined in claim 2, wherein the container body is molded from a thermoplastic polyolefin molding composition.

4. A product dispenser package as defined in claim 1, wherein the product comprises at least one agent selected from the group consisting of: alkali metal hydroxides, alkali metal carbonates, alkali metal bicarbonates, alkali metal sulfates, alkali metal phosphates, silicates, surfactants, nonionic surfactants, organic acids, polyols and alkali metal dichloroisocyanurates, and mixtures of any of the foregoing.

5. A product dispenser package as defined in claim 1, wherein the product further comprises a water soluble binder.

6. A product dispenser package as defined in claim 5, wherein the water soluble binder is selected from the group consisting of water and aqueous solutions or dispersions of one or more water soluble salts.

7. A product dispenser package as defined in claim 5, wherein the water soluble binder is selected from settable gel forming materials which are liquid when heated to temperatures above 40° C. and which set at temperatures of from about 0° C. to about 40° C.

8. A product dispenser package as defined in claim 1, further comprising a sealing layer disposed on a top surface of the product adjacent the open end of the container.

9. A product dispenser package as defined in claim 8, wherein the sealing layer comprises a water soluble or water dispersible material which forms a solid or gel layer at temperatures of from about 0° C. to about 40° C.

10. A product dispenser package as defined in claim 8, wherein the means for maintaining the product in the container comprises a barrier layer disposed in and closing off the open end, releasably secured to the open end of the container body, the barrier layer being selected from the group consisting of water soluble films, water soluble preforms and non-water soluble foils and wherein the barrier layer is releasably secured to the open end by heat sealing, adhesive or mechanical securement methods.

11. A product dispenser package as defined in claim 1, wherein the means for maintaining the product dispenser in the package comprise compression loading of the product in the container body to provide a compacted shape-retaining mass of product.

\* \* \* \* \*